United States Patent
Abraham et al.

(10) Patent No.: US 6,559,105 B2
(45) Date of Patent: May 6, 2003

(54) LUBRICANT COMPOSITIONS CONTAINING ESTER-SUBSTITUTED HINDERED PHENOL ANTIOXIDANTS

(75) Inventors: William D. Abraham, South Euclid, OH (US); Paul E. Adams, Willoughby Hills, OH (US); Gordon D. Lamb, Mickleover (GB); Thomas J. Wolak, Mentor, OH (US); Richard A. Denis, Auburn Township, OH (US); Jody A. Kocsis, Chagrin Falls, OH (US); James P. Roski, Wickliffe, OH (US); Virginia A. Carrick, Chardon, OH (US); Susan V. Cowling, Painesville, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 54 days.

(21) Appl. No.: 09/761,432

(22) Filed: Jan. 16, 2001

(65) Prior Publication Data

US 2002/0006878 A1 Jan. 17, 2002

Related U.S. Application Data

(60) Provisional application No. 60/194,165, filed on Apr. 3, 2000.

(51) Int. Cl.$^7$ ........................................... C10M 141/02
(52) U.S. Cl. ............... 508/186; 508/239; 508/240; 508/391; 508/460; 508/578; 508/584; 508/585; 508/586; 508/373; 508/375; 508/400
(58) Field of Search ................. 508/186, 578, 508/239, 240, 391, 460, 584, 585, 586, 400, 375, 373

(56) References Cited

U.S. PATENT DOCUMENTS

| | | | |
|---|---|---|---|
| 3,285,855 A | 11/1966 | Dexter et al. ................ 252/57 |
| 3,364,250 A * | 1/1968 | Dexter et al. ................ 508/192 |
| 3,657,322 A | 4/1972 | Dexter et al. ................ 260/473 |
| 4,322,303 A | 3/1982 | Rosenberger ............... 252/46.6 |
| 4,536,593 A | 8/1985 | Orban et al. |
| 5,206,414 A | 4/1993 | Evans et al. ................ 560/75 |
| 5,354,486 A | 10/1994 | Evans ........................ 252/57 |
| 5,453,210 A | 9/1995 | Bardasz et al. .............. 252/18 |
| 5,523,007 A | 6/1996 | Kristen et al. ............. 252/32.7 |
| 5,563,291 A | 10/1996 | Kleiner ........................ 560/67 |
| 5,658,865 A | 8/1997 | Yoshida et al. .............. 508/501 |
| 5,696,281 A | 12/1997 | Evans ........................ 560/75 |
| 5,916,851 A | 6/1999 | Hosonuma et al. |
| 5,965,495 A * | 10/1999 | Goto et al. ................. 508/192 |
| 6,310,009 B1 * | 10/2001 | Kocsis et al. ............... 508/186 |

OTHER PUBLICATIONS

European Publication EP 0 620 267, Oct. 19, 1994, equivalent to U.S. patent No. 5,460,741.

* cited by examiner

*Primary Examiner*—Jacqueline V. Howard
(74) *Attorney, Agent, or Firm*—David M. Shold; Michael F. Esposito

(57) ABSTRACT

A composition of an antioxidant of the formula

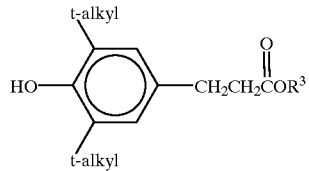

where $R^3$ is an alkyl group of 2 to 6 carbon atoms, and a dispersant or a detergent, is a useful additive package for lubricant compositions.

36 Claims, No Drawings

LUBRICANT COMPOSITIONS CONTAINING ESTER-SUBSTITUTED HINDERED PHENOL ANTIOXIDANTS

CROSS-REFERENCE TO RELATED APPLICATIONS

This application claims priority from U.S. Provisional Application Ser. No. 60/194,165, filed Apr. 3, 2000.

BACKGROUND OF THE INVENTION

The present invention relates to compositions suitable for use as lubricant additives which contain an ester-substituted hindered phenol antioxidant and other additives suitable for lubricants such as a detergent or a dispersant. The present invention provides an economical antioxidant which has good performance properties when used in lubricant formulations especially for heavy duty diesel engines and passenger car crankcase.

U.S. Pat. No. 5,523,007, Kristen et al., Jun. 4, 1996, discloses a lubricant oil composition comprising a diesel engine lubricating oil and, as antioxidant, a compound of the formula

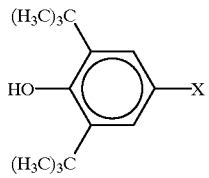

X can be —$CH_2$—$CH_2$—C(=O)—OR and R is a straight chain or branched alkyl radical of the formula —$C_nH_{2n+1}$ wherein n is an integer from 8 to 22.

U.S. Pat. No. 3,285,855, Dexter et al., Nov. 15, 1966, discloses stabilization of organic material with esters containing an alkylhydroxyphenyl group. The ester can have the structure

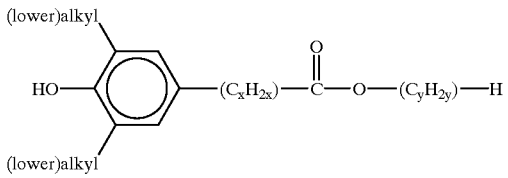

in which x has a value of from 0 to 6, inclusively, and y has a value of from 6 to 30, inclusively. The "lower alkyl" groups can be t-butyl. Organic materials which can be stabilized include, among many others, lubricating oil of the aliphatic ester type, and mineral oil.

U.S. Pat. No. 5,206,414, Evans et al., Apr. 27, 1993, discloses a process for the preparation of compounds of the general formula

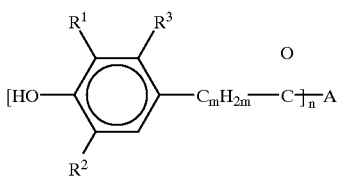

A can be —$OR_4$ where $R_4$ can be $C_2$–$C_{45}$ alkyl.

The present invention provides, among other advantages, a convenient method for obtaining a certain class of hindered phenolic ester antioxidants having particularly useful properties. In particular the antioxidants (shown below), that is, those having an $R^3$ group of 2 to 6 carbon atoms, can be conveniently prepared in a single step. In a preferred synthesis, no trans-esterification reaction is necessary, resulting in a simplified process which leads to fewer byproducts. The antioxidants thus prepared impart excellent thermal and oxidative stability to lubricant formulations and show excellent performance in seal durability tests.

SUMMARY OF THE INVENTION

A composition comprising;
(A) at least one antioxidant of the formula

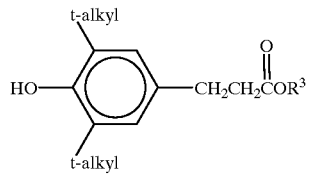

wherein $R^3$ is an alkyl group containing 2 to 6 carbon atoms; and
(B) at least one component selected from the group consisting of dispersants and detergents.

DETAILED DESCRIPTION OF THE INVENTION

Various preferred features and embodiments will be described below by way of non-limiting illustration.

Oil of Lubricating Viscosity

Although not required in all embodiments of this invention, commonly an oil of lubricating viscosity is employed as a medium dissolving or dispersing the other components. Oils of lubricating viscosity include natural and synthetic lubricating oils and mixtures thereof. These lubricants include crankcase lubricating oils for spark-ignited and compression-ignited internal combustion engines, including automobile and truck engines, two-cycle engines, aviation piston engines, and marine and railroad diesel engines. They can also be used in gas engines, stationary power engines, and turbines. Automatic transmission fluids, transaxle lubricants, gear lubricants, metal-working lubricants, hydraulic fluids and other lubricating oil and grease compositions can also benefit from the incorporation therein of the compositions of the present invention.

Natural oils include animal oils and vegetable oils (e.g., castor oil, lard oil) as well as liquid petroleum oils and solvent-treated or acid-treated mineral lubricating oils of the paraffinic, naphthenic or mixed paraffinic-naphthenic types. Oils of lubricating viscosity derived from coal or shale are also useful base oils. Synthetic lubricating oils include hydrocarbon oils such as polymerized and interpolymerized olefins (e.g., polybutylenes, polypropylenes, propylene-isobutylene copolymers, poly(1-hexenes), poly(1-octenes), poly(1-decenes), and mixtures thereof); alkylbenzenes (e.g., dodecylbenzenes, tetradecylbenzenes, dinonylbenzenes, and di(2-ethylhexyl)-benzenes); polyphenyls (e.g., biphenyls, terphenyls, and alkylated polyphenyls), alkylated diphenyl ethers and alkylated diphenyl sulfides and the derivatives, analogs, and homologs thereof.

Alkylene oxide polymers and interpolymers and derivatives thereof where the terminal hydroxyl groups have been modified by esterification, etherification, or similar reaction constitute another class of known synthetic lubricating oils. These are exemplified by the oils prepared through polymerization of ethylene oxide or propylene oxide, the alkyl and aryl ethers of these polyoxyalkylene polymers (e.g., methylpolyisopropylene glycol ether having an average molecular weight of 1,000 diphenyl ether of polyethylene glycol having a molecular weight of 500–1,000, diethyl ether of polypropylene glycol having a molecular weight of 1,000–1,500) or mono- and polycarboxylic esters thereof, for example, the acetic acid esters, mixed $C_3$–$C_8$ fatty acid esters, or the $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, and alkenyl malonic acids) with a variety of alcohols (e.g., butyl alcohol, hexyl alcohol, dodecyl alcohol, 2-ethylhexyl alcohol, ethylene glycol, diethylene glycol monoether, and propylene glycol). Specific examples of these esters include dibutyl adipate, di(2-ethylhexyl sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol, and tripentaerythritol.

Unrefined, refined and rerefined oils (and mixtures of each with each other) of the type disclosed hereinabove can be used in the lubricant compositions of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except that they have been further treated in one or more purification steps to improve one or more properties. Many such purification techniques are known to those of skill in the art such a solvent extraction, acid or base extraction, filtration, percolation, or similar purification techniques. Rerefined oils are obtained by processes similar to those used to obtain refined oils which have been already used in service. Such rerefined oils are also known as reclaimed or reprocessed oils and often are additionally processed by techniques directed to removal of spent additives and oil break-down products.

The aliphatic and alicyclic substituents, as well as aryl nuclei, are generally described as "hydrocarbon-based". The meaning of the term "hydrocarbon-based" as used herein is apparent from the following detailed discussion of "hydrocarbon-based substituent."

As used herein, the terms "hydrocarbon-based substituent," "hydrocarbyl substituent" or "hydrocarbyl group," which are used synonymously, are used in their ordinary sense, which is well-known to those skilled in the art. Specifically, any of these terms refers to a group having a carbon atom directly attached to the remainder of the molecule and having predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring);

(2) substituted hydrocarbon substituents, that is, substituents containing non-hydrocarbon groups which, in the context of this invention, do not alter the predominantly hydrocarbon substituent (e.g., halo (especially chloro and fluoro), hydroxy, alkoxy, mercapto, alkylmercapto, nitro, nitroso, and sulfoxy);

(3) hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

Preferably, the hydrocarbon-based substituents in the compositions of this invention are free from acetylenic unsaturation. Ethylenic unsaturation, when present, preferably will be such that no more than one ethylenic lineage will be present for every 10 carbon-to-carbon bonds in the substituent. The hydrocarbon-based substituents are usually hydrocarbon in nature and more usually, substantially saturated hydrocarbon. As used in this specification and the appended claims, the word "lower" denotes substituents or groups containing up to seven carbon atoms; for example, lower alkoxy, lower alkyl, lower alkenyl, lower aliphatic aldehyde.

The amount of lubricating oil in a fully formulated lubricant of the present invention (including the diluent or carrier oils present in additive packages) is typically 80 to 99.5 weight percent, preferably 85 to 96 weight percent, and more preferably 90 to 95 weight percent. The lubricating oil can also be used to prepare concentrates containing the additives of the present invention in higher concentrations. The amount of such oil in a concentrate is typically 20 to 80 weight percent.

(A) The Antioxidant

The present invention comprises a hindered, ester-substituted phenol such as one represented by the formula

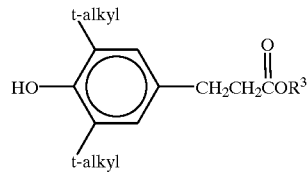

and more preferably

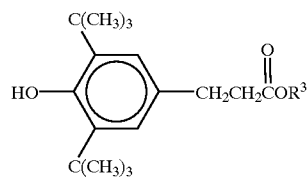

In these structures $R^3$ is a straight chain or branched chain alkyl group containing 2 to 6 carbon atoms, preferably 2 to 4, and more preferably 4 carbon atoms. $R^3$ is most preferably an n-butyl group.

Hindered, ester-substituted phenols of this type can be prepared by heating a 2,6-dialkylphenol with an acrylate ester under base catalysis conditions, such as aqueous KOH.

EXAMPLE 1

To a 5-L round-bottomed 4-necked flask, equipped with a mechanical stirrer, thermal probe, and reflux condenser equipped for distillate removal, is charged 2619 g 2,6-di-t-butylphenol and 17.7 g potassium hydroxide (technical grade). The reaction mixture is heated to 135° C. over 35 minutes and maintained at temperature for 2 hours, removing 9.7 g aqueous distillate. To the reaction mixture is charged 1466 g butyl acrylate dropwise over the course of 90 minutes. The temperature is maintained at 135° C. for up to 2 hours, or until analysis by infrared indicates no further change (by observing peaks at 727 and 768 cm$^{-1}$). To the mixture is charged 103 g magnesium silicate absorbent and 17 g filter aid and stirring is continued for 2 hours, while removing 7.1 g distillate. The mixture is filtered through additional filter aid.

The amount of the above antioxidant in a completely formulated lubricant will typically be 0.05 to 5 percent by weight, preferably 0.25 to 2.0 percent by weight, and more preferably 0.3 to 1.5 percent by weight. Its concentration in a concentrate will be correspondingly increased, to, e.g., 1 to 75 weight percent.

(B-1) The Dispersant

Dispersants are well known in the field of lubricants and include primarily what are sometimes referred to as "ashless" dispersants because (prior to mixing in a lubricating composition) they do not contain ash-forming metals and they do not normally contribute any ash forming metals when added to a lubricant. Dispersants are characterized by a polar group attached to a relatively high molecular weight hydrocarbon chain.

One class of dispersant is Mannich bases. These are materials which are formed by the condensation of a higher molecular weight, alkyl substituted phenol, an alkylene polyamine, and an aldehyde such as formaldehyde. Such materials may have the general structure

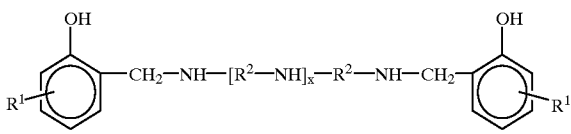

(including a variety of isomers and the like) and are described in more detail in U.S. Pat. No. 3,634,515.

Another class of dispersant is high molecular weight esters. These materials are similar to the above-described Mannich dispersants or the succinimides described below, except that they may be seen as having been prepared by reaction of a hydrocarbyl acylating agent and a polyhydric aliphatic alcohol such as glycerol, pentaerythritol, or sorbitol. Such materials are described in more detail in U.S. Pat. No. 3,381,022.

Other dispersants include polymeric dispersant additives, which are generally hydrocarbon-based polymers which contain polar functionality to impart dispersancy characteristics to the polymer.

A preferred class of dispersants is the carboxylic dispersants. Carboxylic dispersants include succinic-based dispersants, which are the reaction product of a hydrocarbyl substituted succinic acylating agent with an organic hydroxy compound or, preferably, an amine containing at least one hydrogen attached to a nitrogen atom, or a mixture of said hydroxy compound and amine. The term "succinic acylating agent" refers to a hydrocarbon-substituted succinic acid or succinic acid-producing compound (which term also encompasses the acid itself). Such materials typically include hydrocarbyl-substituted succinic acids, anhydrides, esters (including half esters) and halides.

Succinic based dispersants have a wide variety of chemical structures including typically structures such as

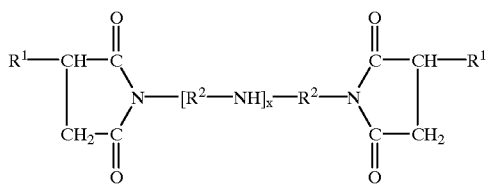

In the above structure, each R$^1$ is independently a hydrocarbyl group, preferably a polyolefin-derived group having an $\overline{M}n$ of 500 or 700 to 10,000. Typically the hydrocarbyl group is an alkyl group, frequently a polyisobutyl group with a molecular weight of 500 or 700 to 5000, preferably 1500 or 2000 to 5000. Alternatively expressed, the R$^1$ groups can contain 40 to 500 carbon atoms and preferably at least 50, e.g., 50 to 300 carbon atoms, preferably aliphatic carbon atoms. The R are alkenyl groups, commonly ethylenyl (C$_2$H4) groups. Such molecules are commonly derived from reaction of an alkenyl acylating agent with a polyamine, and a wide variety of linkages between the two moieties is possible beside the simple imide structure shown above, including a variety of amides and quaternary ammonium salts. Succinimide dispersants are more fully described in U.S. Pat. Nos. 4,234,435 and 3,172,892.

The polyalkenes from which the substituent groups are derived are typically homopolymers and interpolymers of polymerizable olefin monomers of 2 to 16 carbon atoms; usually 2 to 6 carbon atoms.

The olefin monomers from which the polyalkenes are derived are polymerizable olefin monomers characterized by the presence of one or more ethylenically unsaturated groups (i.e., >C=C<); that is, they are mono-olefinic monomers such as ethylene, propylene, 1-butene, isobutene, and 1-octene or polyolefinic monomers (usually diolefinic monomers) such as 1,3-butadiene, and isoprene. These olefin monomers are usually polymerizable terminal olefins; that is, olefins characterized by the presence in their structure of the group >C=CH$_2$. Relatively small amounts of non-hydrocarbon substituents can be included in the polyolefin, provided that such substituents do not substantially interfere with formation of the substituted succinic acid acylating agents.

Each R$^1$ group may contain one or more reactive groups, e.g., succinic groups, thus being represented (prior to reaction with the amine) by structures such as

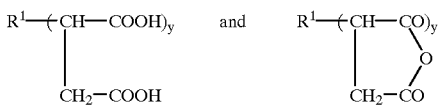

in which y represents the number of such succinic groups attached to the R$^1$ group. In one type of dispersant, y=1. In another type of dispersant, y is greater than 1, preferably greater than 1.3 or greater than 1.4; and most preferably y is equal to or greater than 1.5. Preferably y is 1.4 to 3.5, especially is 1.5 to 3.5 and most especially 1.5 to 2.5. Fractional values of y, of course, can arise because different specific $R^1$ chains may be reacted with different numbers of succinic groups.

The amines which are reacted with the succinic acylating agents to form the carboxylic dispersant composition can be monoamines or polyamines. In either case they will be characterized by the formula $R^4R^5NH$ wherein $R^4$ and $R^5$ are each independently hydrogen, or hydrocarbon, amino-substituted hydrocarbon, hydroxy-substituted hydrocarbon, alkoxy-substituted hydrocarbon, amino, carbamyl, thiocarbamyl, guanyl, and acylimidoyl groups provided that only one of $R^4$ and $R^5$ is hydrogen. In all cases, therefore, they will be characterized by the presence within their structure of at least one H—N<group. Therefore, they have at least one primary (i.e., $H_2N$—) or secondary amino (i.e., H—N<) group. Examples of monoamines include ethylamine, diethylamine, n-butylamine, di-n-butylamine, allylamine, isobutylamine, cocoamine, stearylamine, laurylamine, methyllaurylamine, oleyl-amine, N-methyl-octylamine, dodecylamine, and octadecylamine.

The polyamines from which (C) is derived include principally alkylene amines conforming, for the most part, to the formula

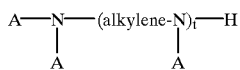

wherein t is an integer preferably less than 10, A is a hydrogen group or a hydrocarbyl group preferably having up to 30 carbon atoms, and the alkylene group is preferably an alkylene group having less than 8 carbon atoms. The alkylene amines include principally methylene amines, ethylene amines, hexylene amines, heptylene amines, octylene amines, other polymethylene amines. They are exemplified specifically by: ethylene diamine, triethylene tetramine, propylene diamine, decamethylene diamine, octamethylene diamine, di(heptamethylene) triamine, tripropylene tetramine, tetraethylene pentamine, trimethylene diamine, pentaethylene hexamine, di(-trimethylene) triamine. Higher homologues such as are obtained by condensing two or more of the above-illustrated alkylene amines likewise are useful. Tetraethylene pentamines is particularly useful.

The ethylene amines, also referred to as polyethylene polyamines, are especially useful. They are described in some detail under the heading "Ethylene Amines" in Encyclopedia of Chemical Technology, Kirk and Othmer, Vol. 5, pp. 898–905, Interscience Publishers, New York (1950).

Hydroxyalkyl-substituted alkylene amines, i.e., alkylene amines having one or more hydroxyalkyl substituents on the nitrogen atoms, likewise are useful. Examples of such amines include N-(2-hydroxyethyl)ethylene diamine, N,N'-bis(2-hydroxy-ethyl)-ethylene diamine, 1-(2-hydroxyethyl) piperazine, mono-hydroxypropyl)-piperazine, di-hydroxypropy-substituted tetraethylene pentamine, N-(3-hydroxypropyl)-tetra-methylene diamine, and 2-heptadecyl-1-(2-hydroxyethyl)-imidazoline.

Higher homologues, such as are obtained by condensation of the above-illustrated alkylene amines or hydroxy alkyl-substituted alkylene amines through amino radicals or through hydroxy radicals, are likewise useful.

The carboxylic dispersant composition (C), obtained by reaction of the succinic acid-producing compounds and the amines described above, may be amine salts, amides, imides, imidazolines as well as mixtures thereof. To prepare the carboxylic dispersant composition (C), one or more of the succinic acid-producing compounds and one or more of the amines are heated, optionally in the presence of a normally liquid, substantially inert organic liquid solvent/diluent at an elevated temperature, generally in the range of 80° C. up to the decomposition point of the mixture or the product; typically 100° C. to 300° C.

The succinic acylating agent and the amine (or organic hydroxy compound, or mixture thereof) are typically reacted in amounts sufficient to provide at least one-half equivalent, per equivalent of acid-producing compound, of the amine (or hydroxy compound, as the case may be). Generally, the maximum amount of amine present will be about 2 moles of amine per equivalent of succinic acylating agent. For the purposes of this invention, an equivalent of the amine is that amount of the amine corresponding to the total weight of amine divided by the total number of nitrogen atoms present. The number of equivalents of succinic acid-producing compound will vary with the number of succinic groups present therein, and generally, there are two equivalents of acylating reagent for each succinic group in the acylating reagents. Additional details and examples of the procedures for preparing the nitrogen-containing compositions of the present invention by reaction of succinic acid-producing compounds and amines are included in, for example, U.S. Pat. Nos. 3,172,892; 3,219,666; 3,272,746; and 4,234,435.

The dispersants may be borated materials. Borated dispersants are well-known materials and can be prepared by treatment with a borating agent such as boric acid. Typical conditions include heating the dispersant with boric acid at 100 to 150° C. The dispersants may also be treated by reaction with maleic anhydride as described in PCT application US99/23940 filed Oct. 13, 1999.

The amount of the dispersant in a completely formulated lubricant, if present, will typically be 0.5 to 10 percent by weight, preferably 1 to 8 percent by weight, and more preferably 3 to 7 percent by weight. Its concentration in a concentrate will be correspondingly increased, to, e.g., 5 to 80 weight percent.

(B-2) The Detergent

Detergents are generally salts of organic acids, which are often overbased. Metal overbased salts of organic acids are widely known to those of skill in the art and generally include metal salts wherein the amount of metal present exceeds the stoichiometric amount. Such salts are said to have conversion levels in excess of 100% (i.e., they comprise more than 100% of the theoretical amount of metal needed to convert the acid to its "normal" or "neutral" salt). They are commonly referred to as overbased, hyperbased or superbased salts and are usually salts of organic sulfur acids, organic phosphorus acids, carboxylic acids, phenols or mixtures of two or more of any of these. As a skilled worker would realize, mixtures of such overbased salts can also be used.

The terminology "metal ratio" is used in the prior art and herein to designate the ratio of the total chemical equivalents of the metal in the overbased salt to the chemical equivalents of the metal in the salt which would be expected to result in the reaction between the organic acid to be overbased and the basic reacting metal compound according to the known chemical reactivity and stoichiometry of the two reactants. Thus, in a normal or neutral salt the metal ratio is one and, in an overbased salt, the metal ratio is greater than one. The over-based salts used as component (A) in this invention usually have metal ratios of at least 3:1. Typically, they have ratios of at least 12:1. Usually they have metal ratios not exceeding 40:1. Typically, salts having ratios of 12:1 to 20:1 are used. Overbased compositions are well known, and the general process for preparing overbased compositions is described in connection with the preparation of overbased Mg saligenin derivatives, below. The optional other overbased compositions can be prepared based on a variety of other well known organic acidic materials including sulfonic acids, carboxylic acids (including substituted salicylic acids), phenols, phosphonic acids, and mixtures of any two or more of these. These materials and methods for overbasing of them are well known from numerous U.S. patents including those mentioned above in connection with the overbasing of the saligenin derivative and need not be further described in detail.

Preferred overbased materials include overbased phenates derived from the reaction of an alkylated phenol, preferably wherein the alkyl group has at least 6 aliphatic carbon atoms. The phenate is optionally reacted with formaldehyde or a sulfurization agent, or mixtures thereof, to provide a bridged or linked structure.

Other preferred overbased materials include metal overbased sulfonates derived from an alkylated aryl sulfonic acid wherein the alkyl group has at least about 15 aliphatic carbon atoms.

Other preferred overbased materials include metal overbased carboxylates derived from fatty acids having at least about 8 aliphatic carbon atoms.

The basically reacting metal compounds used to make these overbased salts are usually an alkali or alkaline earth metal compound (i.e., the Group IA, IIA, and IIB metals excluding francium and radium and typically excluding rubidium, cesium and beryllium), although other basically reacting metal compounds can be used. Compounds of Ca, Ba, Mg, Na and Li, such as their hydroxides and alkoxides of lower alkanols are usually used as basic metal compounds in preparing these overbased salts but others can be used as shown by the prior art referred to herein. Overbased salts containing a mixture of ions of two or more of these metals can be used in the present invention.

Overbased materials are generally prepared by reacting an acidic material (typically an inorganic acid or lower carboxylic acid, preferably carbon dioxide) with a mixture comprising an acidic organic compound, a reaction medium comprising at least one inert, organic solvent (mineral oil, naphtha, toluene, xylene, etc.) for said acidic organic material, a stoichiometric excess of a metal base, and a promoter. The acidic organic compound will, in the present instance, be the above-described saligenin derivative.

The acidic material used in preparing the overbased material can be a liquid such as formic acid, acetic acid, nitric acid, or sulfuric acid. Acetic acid is particularly useful. Inorganic acidic materials can also be used, such as HCl, $SO_2$, $SO_3$, $CO_2$, or $H_2S$, preferably $CO_2$ or mixtures thereof, e.g., mixtures of $CO_2$ and acetic acid.

A promoter is a chemical employed to facilitate the incorporation of metal into the basic metal compositions. The promoters are diverse and are well known in the art. A discussion of suitable promoters is found in U.S. Pat. Nos. 2,777,874, 2,695,910, and 2,616,904. These include the alcoholic and phenolic promoters, which are preferred. The alcoholic promoters include the alkanols of one to twelve carbon atoms such as methanol, ethanol, amyl alcohol, octanol, isopropanol, and mixtures of these. Phenolic promoters include a variety of hydroxy-substituted benzenes and naphthalenes. a particularly useful class of phenols are the alkylated phenols of the type listed in U.S. Pat. No. 2,777,874, e.g., heptylphenols, octylphenols, and nonylphenols. Mixtures of various promoters are sometimes used.

Patents specifically describing techniques for making basic salts of acidic organic compounds generally include U.S. Pat. Nos. 2,501,731; 2,616,905; 2,616,911; 2,616,925; 2,777,874; 3,256,186; 3,384,585; 3,365,396; 3,320,162; 3,318,809; 3,488,284; and 3,629,109.

One useful detergent compound is a metal saligenin derivative. Such materials have been described in detail in U.S. Provisional Application No. 60/194,136. When the metal is magnesium, the compound is represented by the formula

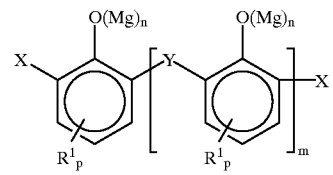

That is, it is a metal salt, and preferably a magnesium salt. In this structure, (Mg) represents a valence of a magnesium ion. (Other valences of the normally divalent Mg ion, not shown, can be satisfied by other anions or by association with additional —O⁻ functionality of the same or additional saligenin derivatives.) Each n is independently 0 or 1, provided that when n is 0, the Mg is replaced by H, that is, to form an unneutralized phenolic —OH group. The average value of n in the composition overall is typically 0.1 to 1.0. That is, the structure represents a partially or completely neutralized magnesium salt, a value of 1.0 corresponding to complete neutralization of each site by the divalent Mg ion. The compound contains one aromatic ring or a multiplicity of aromatic rings linked by "Y" groups, and also "X" groups. The value of "m" can be 0 to 10, which means that the number of such rings will be 1 to 11, although it is to be understood that the upper limit of "m" is not a critical variable. Preferably m is 2 to 9, more preferably 3 to 8 or 4 to 6. It is also permitted that one of the X groups can be —H, particularly if m is 1 or greater. Other suitable metals include alkali metals such as lithium, sodium, or potassium; alkaline earth metals such as calcium or barium; and other metals such as copper, zinc, and tin, and mixtures of such metals.

Most of the rings contain at least one $R^1$ substituent, which is a hydrocarbyl group, preferably an alkyl group, containing 1 to 60 carbon atoms, preferably 7 to 28 carbon atoms, more preferably 9 to 18 carbon atoms. Of course it is understood that $R^1$ will normally comprise a mixture of various chain lengths, so that the foregoing numbers will normally represent an average number of carbon atoms in the $R^1$ groups (number average). Each ring in the structure will be substituted with 0, 1, 2, or 3 such $R^1$ groups (that is, p is 0, 1, 2, or 3), most typically 1, and of course different rings in a given molecule may contain different numbers of such substituents. At least one aromatic ring in the molecule must contain at least one $R^1$ group, and the total number of carbon atoms in all the $R^1$ groups in the molecule should be at least 7, preferably at least 12.

In the above structure the X and Y groups may be seen as groups derived from formaldehyde or a formaldehyde source, by condensative reaction with the aromatic molecule. The relative amounts of the various X and Y groups depends to a certain extent on the conditions of synthesis of the molecules. While various species of X and Y may be present in the molecules in question, the commonest species comprising X are —CHO (aldehyde functionality) and —CH₂OH (hydroxymethyl functionality); similarly the commonest species comprising Y are —CH₂— (methylene bridge) and —CH₂OCH₂— (ether bridge). The relative molar amounts of these species in a sample of the above material can be determined by $^1H/^{13}C$ NMR as each carbon and hydrogen nucleus has a distinctive environment and produces a distinctive signal. (The signal for the ether linkage, —CH$_2$OCH$_2$— must be corrected for the presence of two carbon atoms, in order to arrive at a correct calculation of the molar amount of this material. Such a correction is well within the abilities of the person skilled in the art.)

In a preferred embodiment, X is at least in part —CHO and such —CHO groups comprise at least 10, 12, or 15 mole percent of the X and Y groups. Preferably the —CHO groups comprise 20 to 60 mole percent of the X and Y groups and more preferably 25 to 40 mole percent of the X and Y groups.

In another embodiment, X is at least in part —CH$_2$OH and such —CH$_2$OH groups comprise 10 to 50 mole percent of the X and Y groups, preferably 15 to 30 mole percent of the X and Y groups.

In an embodiment in which m is non-zero, Y is at least in part —CH$_2$— and such —CH$_2$— groups comprise 25 to 55 mole percent of the X and Y groups, preferably 32 to 45 mole percent of the X and Y groups.

In another embodiment Y is at least in part —CH$_2$OCH$_2$— and such —CH$_2$OCH$_2$— groups comprise 5 to 20 mole percent of the X and Y groups, and preferably 10 to 16 mole percent of the X and Y groups.

The above-described compound is preferably a magnesium salt and, indeed, the presence of magnesium during the preparation of the condensed product is believed to be important in achieving the desired ratios of X and Y components described above. The number of Mg ions in the composition is characterized by an average value of "n" of 0.1 to 1.0, preferably 0.2 or 0.4 to 0.9, and more preferably 0.6 to 0.8, which correspond to 20–100%, 20 or 40–90%, or 60–80% neutralization by Mg. Since Mg is normally a divalent ion, it can neutralize up to two phenolic hydroxy groups. Those two hydroxy groups may be on the same or on different molecules. If the value of n is less than 1.0, this indicates that the hydroxy groups are less than completely neutralized by Mg ions. Alternatively, each Mg ion could be associated with one phenolic anion and an ion of another type such as a hydroxy (OH$^-$) ion or carbonate ion (CO$_3^-$), while still providing an n value of 1.0. The specification that the average value of n is 0.1 to 1.0 is not directly applicable to overbased versions of this material (described below and also a part of the present invention) in which an excess of Mg or another cation can be present. It should be understood that, even in an overbased material, some fraction of the phenolic OH groups may not have reacted with the magnesium and may retain the OH structure.

It is understood that in a sample of a large number of molecules, some individual molecules will exist which deviate from these parameters: for instance, there may be some molecules containing no R$^1$ groups whatsoever. Likewise, some fraction of molecules may contain only one (or even zero) X groups, while some may contain more than two X groups. And some fraction of the aromatic groups may be linked by Y groups to more than two neighboring aromatic groups. These molecules could be considered as impurities, and their presence will not negate the present invention so long as the majority (and preferably the substantial majority) of the molecules of the composition are as described. In any event, compositions exhibiting this type of variability are to be construed as encompassed by the present invention and the description that a material is "represented by" the formula shown. There is believed to be a reasonable possibility that a significant fraction of the polynuclear molecules of the present invention may bear only a single X group. In order to explicitly account for this possibility, it is to be understood that in the materials of an embodiment of the present invention, especially if m is 1 or greater, one (but preferably not both) of the X groups in the above structures can be —H.

The above-described component can be prepared by combining a phenol substituted by the above-described R$^1$ group with formaldehyde or a source of formaldehyde and magnesium oxide or magnesium hydroxide under reactive conditions, in the presence of a catalytic amount of a strong base. Common reactive equivalents of formaldehyde includes paraformaldehyde, paraldehyde, trixoane, formalin and methal. For convenience, paraformaldehyde is preferred.

The relative molar amounts of the substituted phenol and the formaldehyde can be important in providing products with the desired structure and properties. It is preferred that the substituted phenol and formaldehyde are reacted in equivalent ratios of 1:1 to 1:3 or 1.4, more preferably 1:1.1 to 1:2.9 or 1:1.4 to 1:2.6, and still more preferably 1:1.7 to 1:2.3. Thus under preferred conditions there will be about a 2:1 equivalent excess of formaldehyde. (One equivalent of formaldehyde is considered to correspond to one H$_2$CO unit; one equivalent of phenol is considered to be one mole of phenol.)

The strong base is preferably sodium hydroxide or potassium hydroxide, and can be supplied in an aqueous solution.

The process can be conducted by combining the above components with an appropriate amount of magnesium oxide or magnesium hydroxide with heating and stirring. A diluent such as mineral oil or other diluent oil can be included to provide for suitable mobility of the components. An additional solvent such as an alcohol can be included if desired, although it is believed that the reaction may proceed more efficiently in the absence of additional solvent. The reaction can be conducted at room temperature or, preferably, a slightly elevated temperature such as 35–120° C., 70–110° C., or 90–100° C., and of course the temperature can be increased in stages. When water is present in the reaction mixture it is convenient to maintain the mixture at or below the normal boiling point of water. After reaction for a suitable time (e.g., 30 minutes to 5 hours or 1 to 3 hours) the mixture can be heated to a higher temperature, preferably under reduced pressure, to strip off volatile materials. Favorable results are obtained when the final temperature of this stripping step is 100 to about 150° C., preferably 120 to about 145° C.

Reaction under the preferred conditions described above leads to a product which has a relatively high content of —CHO substituent groups, that is, 10%, 12%, and preferably 15% and greater. Such materials, when used as detergents in lubricating compositions, exhibit good upper piston cleanliness performance, low Cu/Pb corrosion, and good compatibility with seals. Use of metals other than magnesium in the synthesis typically leads to a reduction in the content of —CHO substituent groups.

EXAMPLE 2

To a 5-L, 4-necked round bottom flask equipped with stirrer, stopper, thermowell, and reflux condenser, the following are charged: 670 g diluent oil (mineral oil), 1000 g dodecyl phenol, and a solution of 3 g NaOH in 40 g water. The mixture is heated to 35° C. with stirring (350 r.p.m.). When 35° C. is attained, 252 g of paraformaldehyde (90%) are added to the mixture and stirring is continued. After 5 minutes, 5 g of MgO and 102 g of additional diluent oil are added. The mixture is heated to 79° C. and held at temperature for 30 minutes. A second increment of 58 g MgO is added and the batch further heated and maintained at 95–100° C. for 1 hour. Thereafter the mixture is heated to 120° C. under a flow of nitrogen at 28 L/hr (1.0 std. ft$^3$/hr.). When 120° C. is reached, 252 g diluent oil is added, and the mixtures is stripped for 1 hour at a pressure of 2.7 kPa (20 torr) at 120° C. for 1 hour and then filtered.

The resulting product is analyzed and contains 1.5% by weight magnesium and has a Total Base Number (TBN) of 63. Analysis of the product by ID and 2D $^1$H/$^{13}$C NMR reveals an aldehyde content of 29 mole %, a methylene bridge content of 38 mole %, an ether bridge content of 12 mole %, and a hydroxymethyl content of 21 mole %.

The material prepared by the above process can be further treated by boration or by overbasing. Borated compositions are prepared by reaction of the above-described saligenin derivative one or more boron compounds. Suitable boron compounds include boric acid, borate esters, and alkali or mixed alkali metal and alkaline earth metal borates. These metal borates are generally a hydrated particulate metal borate and they, as well as the other borating agents, are known in the art and are available commercially. Typically the saligenin derivative is heated with boric acid at 50–100° C.

The material can also be overbased. Overbased salts of organic acids generally, and methods of their synthesis, have been described above and are widely known to those of skill in the art. The magnesium saligenin derivative can be overbased using additional Mg metal or using a different metal.

EXAMPLE 3

Mg Saligenin Derivative Overbased with Ca

Into a 2 L four-necked flask equipped with stirrer, thermowell, reflux condenser, and a subsurface tube, is charged 1000 g of the product of Example 2 (Mg saligenin derivative in diluent oil), 50 g of a mixture of isobutyl and amyl alcohols, 100 g of methanol, and 74 g of Ca(OH)$_2$. A solution of 1 g acetic acid in 4 g water is added to the flask and the contents are held, with stirring, at 44° C. for 30 minutes. Carbon dioxide is blown through the mixture for 1 hour or longer, at 14 L/hr (0.5 std. ft$^3$/hr.) until a direct base number of 15 is obtained. The mixture is heated to 120° C. under a nitrogen flow of 28 L/hr (1.0 std. ft$^3$/hr.) for 1 hour, to strip volatiles. The resulting mixture is filtered and determined to have a TBN of 142 and to contain 3% Ca and 1.4% Mg by weight. NMR analysis reveals 30% aldehyde functionality, 39% methylene coupling, 17% ether coupling, and 14% hydroxymethyl functionality.

EXAMPLE 4

Mg Overbased Saligenin Derivative

Into a 2-liter, four-necked flask equipped with stirrer, thermowell, reflux condenser, and subsurface tube, is charged 1000 g of the product of example 2, 50 g of a mixture of isobutyl and amyl alcohols, and 63 g MgO. The mixture is heated, with stirring, to 50° C. A solution of 130 g of stearic acid and 100 g of dil oil is added. The mixture is heated to 70° C. and held at this temperature for 3 hours. The mixture was cooled to 60° C. To the mixture, 100 g of methanol and 7 g acetic acid are added. Carbon dioxide is blown through the mixture for over 3 hours at 28 L/hr (0.5 std. ft$^3$/hr) until a direct base number of less than 5 is obtained for the mixture. The mixture is stripped to 120° C. under a carbon dioxide flow of 28 L/hr (0.5 std. ft$^3$/hr) and held at this temperature for 1 hour under nitrogen flow at 14 L/hr (0.5 std. ft$^3$/hr). The product is filtered and determined to have a TBN of 130 and to contain 2.8 weight % magnesium. Analysis reveals 32% aldehyde functionality, 41% methylene coupling, 12% ether coupling, and 15% hydroxymethyl functionality.

The detergents generally can also be borated by treatment with a borating agent such as boric acid. Typical conditions include heating the detergent with boric acid at 100 to 150° C., the number of equivalents of boric acid being roughly equal to the number of equivalents of metal in the salt. U.S. Pat. No. 3,929,650 discloses borated complexes and their preparation.

The amount of the detergent component in a completely formulated lubricant, if present, will typically be 0.5 to 10 percent by weight, preferably 1 to 7 percent by weight, and more preferably 1.2 to 4 percent by weight. Its concentration in a concentrate will be correspondingly increased, to, e.g., 5 to 65 weight percent.

(C) The Metal Salt of a Phosphorus Acid

Metal salts of the formula

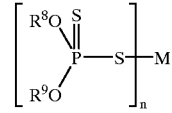

wherein $R^8$ and $R^9$ are independently hydrocarbyl groups containing 3 to 30 carbon atoms are readily obtainable by the reaction of phosphorus pentasulfide ($P_2S_5$) and an alcohol or phenol to form an O,O-dihydrocarbyl phosphorodithioic acid corresponding to the formula

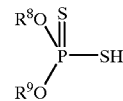

The reaction involves mixing at a temperature of 20° C. to 200° C., four moles of an alcohol or a phenol with one mole of phosphorus pentasulfide. Hydrogen sulfide is liberated in this reaction. The acid is then reacted with a basic metal compound to form the salt. The metal M, having a valence n, generally is aluminum, lead, tin, manganese, cobalt, nickel, zinc, or copper, and most preferably zinc. The basic metal compound is thus preferably zinc oxide, and the resulting metal compound is represented by the formula

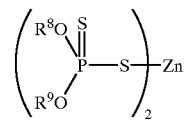

The $R^8$ and $R^9$ groups are independently hydrocarbyl groups that are preferably free from acetylenic and usually also from ethylenic unsaturation. They are typically alkyl, cycloalkyl, aralkyl or alkaryl group and have 3 to 20 carbon atoms, preferably 3 to 16 carbon atoms and most preferably up to 13 carbon atoms, e.g., 3 to 12 carbon atoms. The alcohols which react to provide the $R^8$ and $R^9$ groups can be one or more primary alcohols, one or more secondary alcohols, a mixture of secondary alcohol and primary alcohol. A mixture of two secondary alcohols such as isopropanol and 4-methyl-2-pentanol is often desirable.

Such materials are often referred to as zinc dialkyldithiophosphates or simply zinc dithiophosphates. They are well known and readily available to those skilled in the art of lubricant formulation.

The amount of the metal salt of a phosphorus acid in a completely formulated lubricant, if present, will typically be 0.1 to 5 percent by weight, preferably 0.3 to 2 percent by weight, and more preferably 0.5 to 1.5 percent by weight. Its concentration in a concentrate will be correspondingly increased, to, e.g., 5 to 60 weight percent.

EXAMPLE 5

Fully Formulated Lubricant

A fully formulated lubricant is prepared in a mineral oil base fluid (containing viscosity modifier). The lubricant contains, in addition to 1.0 percent by weight (active chemical) of the phenolic antioxidant of Example 1, the following additional components: a polyolefin amide alkeneamine dispersant, 3.6%; zinc alkyl dithiophosphate, 1.1%; overbased sulfonate detergent(s), 1.6%; overbased phenate detergent(s) 1.5%, and 100 p.p.m. polydimethylsiloxane antifoam agent. The lubricant has a total base number of 10.1 and contains 1.4% sulfated ash.

EXAMPLE 6

Fully Formulated Lubricant

A fully formulated lubricant is prepared in a mineral oil base fluid (containing viscosity modifier). The lubricant contains, in addition to 1.0 percent by weight (active chemical) of the phenolic antioxidant of Example 1, the following additional components: 0.5% of an alkenyl ester sulfide inhibitor, a polyolefin amide alkeneamine dispersant, 3.6%; polyolefin anhydride, 0.3%; zinc alkyl dithiophosphate, 1.1%; overbased sulfonate detergent(s), 1.8%; overbased phenate detergent(s) 1.3%, and 100 p.p.m. polydimethylsiloxane antifoam agent. The lubricant has a total base number of 11.1 and contains 1.5% sulfated ash.

EXAMPLE 7

As an illustration of the effectiveness of the present antioxidant in minimizing deposit formation, a hot tube test was performed. This test compares a sample of lubricant containing the presently claimed antioxidant (where the $R^3$ alkyl group contains 4 carbon atoms) with a lubricant containing an antioxidant in which the $R^3$ group contains 8 carbon atoms. The hot tube test simulates deposit-forming tendencies in crankcase lubricants. A sample of lubricant is fed continuously along with air through a small glass tube at elevated temperatures for 16 hours. At the conclusion of the test the deposits on the tube are visually rated. Higher ratings indicate less deposits (greater thermal stability). A rating of 7.0 or greater on a scale of 10 is considered acceptable. Although at high concentrations (1.0 or 1.5 percent by weight of the antioxidant) both samples provide ratings of 7.5 (or in one run 8.0), at the more critical, lower concentration of 0.5 percent, the material of the present invention exhibits improved performance.

Test Samples: Both samples contain about 53 parts of a 145 N oil and about 24 parts of a 600 N oil; 14.3 parts of commercial heavy duty diesel and other additive(s); 7.2 parts of a viscosity improver; and 1.1 parts of an overbased calcium sulfonate detergent (all the foregoing amounts uncorrected for the presence of conventional diluent oil). Formulation A (inventive) contains in addition 0.5% of the $C_4$ alkyl ester of 3-(4-hydroxy-3,5-di-t-butylphenyl)-propanoic acid. Formulation B (comparative) contains 0.5% of the $C_8$ alkyl ester of 3-(4-hydroxy-3,5-di-t-butylphenyl)-propanoic acid.

The test results are shown in the following table:

| Formulation | A | B (comparative) |
|---|---|---|
| Rating at 280° C. | 7.5 | 6.5 |
| Rating at 290° C. | 7.5 | 4.5 |

The compositions of the present invention may also include, or exclude, conventional amounts of other components which are commonly found in lubricating compositions. For instance, corrosion inhibitors, extreme pressure agents, and anti-wear agents include but are not limited to dithiophosphoric esters; chlorinated aliphatic hydrocarbons; boron-containing compounds including borate esters; and molybdenum compounds. Viscosity improvers include but are not limited to polyisobutenes, polymethyacrylate acid esters, polyacrylate acid esters, diene polymers, polyalkyl styrenes, alkenyl aryl conjugated diene copolymers, polyolefins and multifunctional viscosity improvers. Pour point depressants are a particularly useful type of additive, often included in the lubricating oils described herein usually comprising substances such as polymethacrylates, styrene-based polymers, crosslinked alkyl phenols, or alkyl naphthalenes,. See for example, page 8 of "Lubricant Additives" by C. V. Smalheer and R. Kennedy Smith (Lesius-Hiles Company Publishers, Cleveland, Ohio, 1967). Anti-foam agents used to reduce or prevent the formation of stable foam include silicones or organic polymers. Examples of these and additional anti-foam compositions are described in "Foam Control Agents", by Henry T. Kerner (Noyes Data Corporation, 1976), pages 125–162. Additional antioxidants can also be included, typically of the aromatic amine or hindered phenol type. These and other additives which may be used in combination with the present invention are described in greater detail in U.S. Pat. No. 4,582,618 (column 14, line 52 through column 17, line 16, inclusive).

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil which may be customarily present in the commercial material, unless otherwise indicated. It is to be understood that the upper and lower amount, range, and ratio limits set forth herein may be independently combined. As used herein, the expression "consisting essentially of" permits the inclusion of substances which do not materially affect the basic and novel characteristics of the composition under consideration.

What is claimed is:

1. A composition comprising;
    (A) at least one antioxidant of the formula

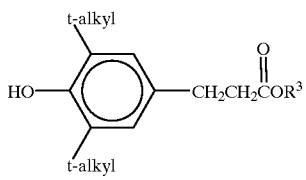

wherein $R_3$ is an alkyl group containing 2 to 6 carbon atoms; and
    (B) at least one component selected from the group consisting of dispersants and detergents.

2. The composition of claim 1 wherein each t-alkyl group is a t-butyl group.

3. The composition of claim 2 wherein $R^3$ contains 4 carbon atoms.

4. The composition of claim 3 wherein $R^3$ is n-butyl.

5. The composition of claim 1 wherein component (B) comprises (B-1) a carboxylic dispersant.

6. The composition of claim 5 wherein the carboxylic dispersant (B-1) comprises the reaction of a hydrocarbon substituted succinic acid-producing compound with at least about one-half equivalent, per equivalent of acid producing compound, of an organic hydroxy compound, or an amine containing at least one hydrogen attached to a nitrogen atom, or a mixture of said hydroxy compound and amine.

7. The composition of claim 6 wherein the succinic acid-producing compound contains an average of at least about 50 aliphatic carbon atoms in the substituent.

8. The composition of claim 6 wherein the succinic acid-producing compound is selected from the group consisting of succinic acids, anhydrides, esters and halides.

9. The composition of claim 6 wherein the hydrocarbon substituent of the succinic acid-producing compound is derived from a polyolefin having an $\overline{M}n$ of about 700 to about 10,000.

10. The composition of claim 6 wherein the hydrocarbon substituent of the succinic acid-producing compound is derived from a polyolefin having an $\overline{M}n$ of about 1500 to about 5000 and wherein there are greater than about 1.3 succinic groups per hydrocaron substituent.

11. The composition of claim 6 wherein the amine reacted with the succinic acid-producing compound is characterized by formula $$R^4R^5NH$$

wherein $R^4$ and $R^5$ are each independently hydrogen, hydrocarbyl, amino-substituted hydrocarbyl, hydroxy-substituted hydrocarbyl, alkoxy-substituted hydrocarbyl, thiocarbamylalkyl, acylimidoylalkyl, or thioureylalkyl groups, provided that at most one of $R^4$ and $R^5$ is hydrogen.

12. The composition of claim 6 wherein the amine reacted with the succinic acid-producing compound is a polyamine.

13. The composition of claim 1 wherein the dispersant (B-1) is treated with a borating agent.

14. The composition of claim 1 wherein component (B) comprises (B-2) a metal overbased detergent composition.

15. The composition of claim 14 wherein the metal overbased detergent composition is selected from the group consisting of
    (a) a metal overbased phenate derived from the reaction of an alkylated phenol wherein the alkyl group has at least 6 aliphatic carbon atoms,
    (b) a metal overbased sulfonate derived from an alkylated aryl sulfonic acid wherein the alkyl group has at least 15 aliphatic carbon atoms, and
    (c) a metal overbased carboxylate derived from fatty acids having at least 8 aliphatic carbon atoms.

16. The composition of claim 14 wherein the metal is an alkali metal or alkaline earth metal.

17. The composition of claim 16 wherein the alkaline earth metal is calcium or magnesium.

18. The composition of claim 16 wherein the alkali metal is lithium or sodium.

19. The composition of claim 15 wherein the metal overbased detergent composition is treated with a borating agent.

20. The composition of claim 1 wherein component B comprises both (B-1) a dispersant and (B-2) a detergent.

21. The composition of claim 1 further comprising an oil of lubricating viscosity.

22. The composition of claim 1 further comprising (C) at least one metal salt of a phosphorus acid, represented by the formula

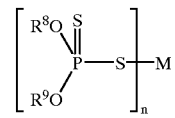

wherein $R^8$ and $R^9$ are each independently hydrocarbyl groups containing 3 to about 30 carbon atoms, M is a metal, and n is an integer equal to the valence of M.

23. The composition of claim 22 wherein the hydrocarbyl groups of component (C) comprise alkyl, cycloalkyl, aralkyl or alkaryl groups.

24. The composition of claim 22 wherein the hydrocarbyl groups are alkyl groups that contain up to 13 carbon atoms.

25. The composition of claim 22 wherein the metal M comprises aluminum, lead, tin, manganese, cobalt, nickel, zinc, or copper.

26. The composition of claim 22 wherein the metal M comprises zinc.

27. The composition of claim 22 wherein the metal is zinc and the phosphorus acid is prepared by reacting phosphorus pentasulfide with at least one secondary alcohol.

28. The composition of claim 22 wherein the metal is zinc and the phosphorus acid is prepared by reacting phosphorus pentasulfide with a mixture of at least one secondary alcohol and one primary alcohol.

29. The composition of claim 22 wherein the metal is zinc and the phosphorus acid is prepared by reacting phosphorus pentasulfide with a mixture of isopropanol and 4-methyl-2-pentanol.

30. The composition of claim 1 wherein component (B) comprises at least one compound represented by the formula

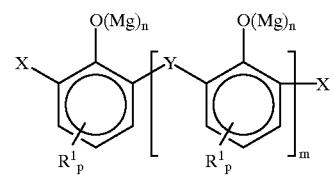

wherein each X independently is —CHO or —CH$_2$OH,
    each Y independently is —CH$_2$— or —CH$_2$OCH$_2$—;
    each $R^1$ is independently a hydrocarbyl group containing 1 to about 60 carbon atoms;

(Mg) represents a valence of a magnesium ion;

each n is independently 0 or 1, the average value of n in the composition being about 0.1 to 1.0; provided that when n is 0, the Mg is replaced by H;

m is 0 to about 10;

and each p is independently 0, 1, 2, or 3;

provided that at least one aromatic ring contains an $R^1$ substituent and that the total number of carbon atoms in all $R^1$ groups is at least 7;

further provided 1 of the X groups can be —H.

31. The composition of claim 30 wherein in the structure shown each aromatic ring is substituted by one $R^1$ group which is an alkyl group containing 7 to about 28 carbon atoms.

32. The composition of claim 30 wherein the average value of n is about 0.2 to 0.9.

33. The composition of claim 30 wherein m is 3 to 8.

34. The composition of claim 30 wherein X is at least in part —CHO and such —CHO groups comprise at least 10 mole percent of the X and Y groups.

35. The composition of claim 34 wherein the —CHO groups comprise about 20 to about 60 mole percent of the X and Y groups.

36. The composition of claim 30 wherein the structure shown is treated with a borating agent.

* * * * *